United States Patent [19]

Bilow et al.

[11] 4,188,337

[45] Feb. 12, 1980

[54] NITRILE SUBSTITUTED POLYIMIDE PRECURSORS

[75] Inventors: Norman Bilow, Los Angeles; Abraham L. Landis, Northridge; Leroy J. Miller, Canoga Park, all of Calif.

[73] Assignee: Hughes Aircraft Company, Culver City, Calif.

[21] Appl. No.: 929,046

[22] Filed: Jul. 28, 1978

Related U.S. Application Data

[62] Division of Ser. No. 702,818, Jul. 6, 1976, Pat. No. 4,129,570.

[51] Int. Cl.$^2$ ............................................. C07C 121/78
[52] U.S. Cl. ................................................ 260/465 D
[58] Field of Search .......... 260/465 D, 326 N, 326 C, 260/326 S

[56] References Cited

U.S. PATENT DOCUMENTS

| | | | |
|---|---|---|---|
| 3,845,018 | 10/1974 | Bilow et al. | 260/326 C |
| 3,890,274 | 6/1975 | D'Alelio | 260/326 C |
| 3,897,395 | 7/1975 | D'Alelio | 260/326 N |
| 3,998,786 | 12/1976 | D'Alelio | 260/47 CP |

*Primary Examiner*—Dolph H. Torrence
*Attorney, Agent, or Firm*—Booker T. Hogan, Jr.; W. H. MacAllister

[57] ABSTRACT

The present invention is directed to a novel class of polynitrile (polycyano) substituted polyimide oligomers and the polyamic acid or ester precursors thereof. The nitrile groups on the oligomers allow the compounds to be cured through addition reactions which result in little or no outgassing. In addition, these oligomers are curable with heat in the presence of catalysts such as those which induce cyano trimerizations. The fully cured polyimides derived from these oligomers have excellent thermal and mechanical properties at high temperatures.

5 Claims, No Drawings

NITRILE SUBSTITUTED POLYIMIDE PRECURSORS

The invention herein described was made in the course of or under a contract with the United States Air Force.

This is a division of application Ser. No. 702,818, filed July 6, 1976, now U.S. Pat. No. 4,129,570.

BACKGROUND OF THE INVENTION

The patent literature has fully disclosed the preparation of polyimide oligomers and precursors by reaction of aromatic compounds, such as pyromellitic acid and 3,3',4,4'-benzophenonetetracarboxylic acid, lower alkyl esters thereof, or the corresponding dianhydrides, with aromatic diamines. The fully cured polyimide compounds are relatively insoluble and intractable materials. When they are used as laminating resins, adhesives, etc., they are applied in the form of the polyamic acid or ester precursor and then cured. This cure step produces water or alcohol as byproduct, resulting in the formation of undesirable voids in the final composite assembly.

SUMMARY OF THE PRESENT INVENTION

Our invention is directed to a class of polyimides and precursors thereof. The polyimide precursors may be applied as coatings on wires or other substrates, as adhesives, or as laminating resins. In addition, they may be used to form addition copolymers with compounds such as terephthalonitrile N,N'-dioxide. In either event, the final products, e.g., coatings, cured adhesives, laminates, etc., have very low void contents as well as excellent thermal and physical properties.

DETAILED DESCRIPTION OF THE INVENTION

The novel polyimide compounds of this invention have the general formula:

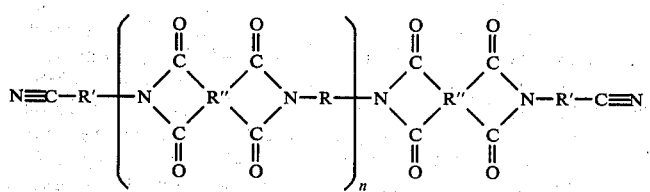

I wherein n is an average value from 1 to about 10, preferably from 1 to about 4, when in prepolymeric or uncured form, R is arylene ether, arylene ketone, diarylene methane, arylene sulfone, or arylene thioether or the nitrile substituted derivative thereof, R' is arylene, arylene thioether, diarylene methane, or arylene ether, R" is

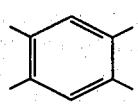

II

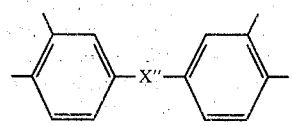

III and X" is C=O, CH$_2$, O, S, or a bond or nitrile substituted derivatives thereof.

Our invention also includes polyimide precursors of the formula

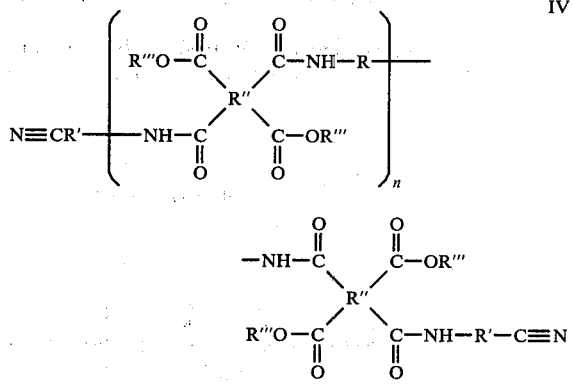

IV wherein R, R', R" and n are as defined above, and R''' is H or lower alkyl, e.g. methyl, propyl, butyl and preferably ethyl. R and R" may contain pendent cyano groups.

The precursors of Formula IV can be prepared in accordance with the processes of the prior art by reacting a stoichiometric excess of an aromatic tetracarboxylic acid, a lower alkyl tetra ester thereof, or the corresponding dianhydride with a compound of the formula H$_2$N—R—NH$_2$, wherein R is arylene ether, arylene ketone, diarylene methane, arylene sulfone, arylene thioether or nitrile substituted derivatives thereof. In order to increase the tractability and solubility of the nitrile substituted products of this invention, R will preferably contain two or more ether or thioether linkages between arylene radicals and/or pendant arylene substituents on an aryl ether radical. Compounds of particular interest are those in which R corresponds to the following:

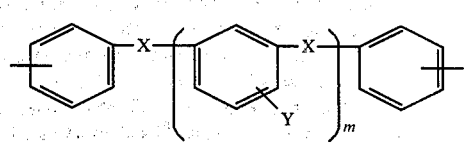

V wherein X is O or S, Y is H or C≡N, m is a value from 0 to about 4, and the amino groups of Formula IV are meta or para to the ether or thioether linkages. We prefer compounds wherein the amino groups are in the meta positions because they have lower melting points and are more tractable. In any given molecule in which m is 2 or more, the Y substituents may be the same or different. Representative compounds having pendant arylene groups are 3,3'-diamino-5-phenyl diphenyl ether, and 3,3'-diamino-5-phenoxy diphenyl ether. Other typical diamines include 1-(3-aminophenoxy)-3-(4-aminophenoxy) benzene, 1,3-bis(3-aminophenoxy)benzene, and 1-(4-aminophenoxy)-3-(4-aminophenoxy)benzene. We have had particularly good results with 1,3-di(3-aminophenoxy)benzene in producing nitrile substituted polyimides which have good solubility and tractability.

Utilizing a dianhydride for illustration, the reaction proceeds according to the following equation.

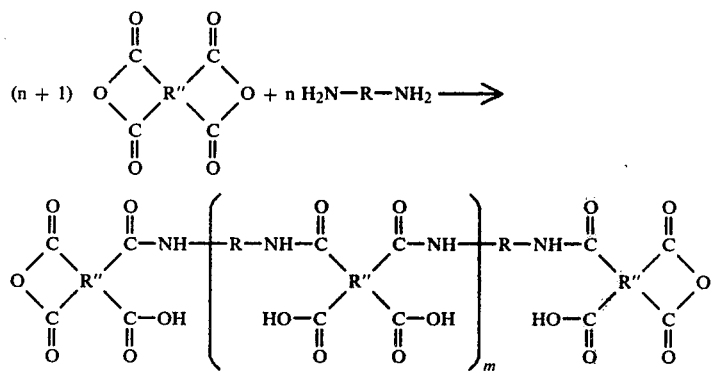

wherein n is one or greater and m is zero or greater. The number of repeating units depends upon the ratio of the tetracarboxylic acid or its derivative to the arylene diamine according to the following chart:

| m | Molar Ratio of Carboxylic Acid Derivative to Diamine |
|---|---|
| 0 | 2.00 |
| 1 | 1.50 |
| 2 | 1.33 |
| 3 | 1.25 |
| m = ∞ | 1.00 |

As illustrated above, the anhydride-capped polyamic acid or the corresponding acid- or ester-capped analog is reacted with a compound of the following formula:

$H_2N$—Arylene—$C\equiv N$        VIII wherein arylene is phenylene, naphthylene, or oxydiphenylene. We prefer m-aminobenzonitrile, 3-amino-3'-cyanodiphenyl, 4-amino-3'-cyanodiphenyl, 3-amino-4'-cyanodiphenyl, 1-(3-cyanophenoxy)-3-(3-aminophenoxy)benzene, 1-(3-cyanophenoxy)-4-(3-aminophenoxy)benzene, or 1-(3-cyanophenoxy)-3-(4-aminophenoxy)benzene because the meta substitutions provide oligomers with lower melting points, better solubility, and better melt flow properties. The precursor and aminoarylnitrile may be reacted in a solvent such as dimethylformamide at elevated temperatures, e.g., from about 60° C. to about 100° C. The reaction produces a reasonable yield of the polyamic acid in from about 1 hour to about 4 hours. The dimethylformamide solvent may then be removed and the polyamic acid product diluted with the imidization agent such as acetic anhydride or a benzene-cresol mixture. When the latter is used, the reaction may be continued until water evolution ceases, and this can be seen by collecting the evolved water in an azeotropic trap. In this latter mixture the reaction temperature is regulated by the boiling point of the benzene-cresol mixture. After the reaction is completed, the solution is cooled and the solvent removed.

Some aminoarylnitriles (VIII) are known compounds. For instance, the m-aminobenzonitrile is commercially available from Mide Chem. Co. of New York. The others may be prepared by standard procedures, starting with known compounds.

We have obtained excellent results with the di-, tri-, or poly nitrile substituted polyimides of this invention. For example, they may be reacted with terephthalonitrile N,N'-dioxide to form copolymers which make excellent laminating resins and molding resins. Even more surprising, the nitrile substituted polyimides may be used as such in the presence of a catalyst such as tetraphenyl tin to prepare laminates or adhesives of excellent physical properties.

The following examples are set forth to illustrate the present invention:

EXAMPLE I

A solution of 1, 3-di(3-aminophenoxy)benzene (14.0 grams, 0.0480 mole) in 75 ml of dry dimethylformamide was added to a rapidly stirring solution of benzophenonetetracarboxylic dianhydride (31.8 grams, 0.0960 mole) in 125 ml of dimethylformamide. The solution then was heated at gentle reflux for 45 minutes. The heating was discontinued and solid 3-aminobenzonitrile (12.45 grams, 0.106 mole) was added all at once and the solution once more was heated at gentle reflux for 45 minutes. The solvent then was removed using a rotary film evaporator, acetic anhydride (410 ml) was added to the residue and the mixture was stirred at room temperature for 16 hours. After heating the mixture at reflux for 3 hours, the slurry was cooled to room temperature and slowly added to 2 liters of absolute ethanol. The precipitated resin was separated by centrifugation, dispersed in 600 ml of ethanol, filtered through a Buchner funnel and pressed dry using a rubber dam. The product was dried in a vacuum oven at 80° C. and yielded 35.3 grams of product.

EXAMPLE II

A laminate was fabricated from the resin of Example I by the following procedure. A solution of the nitrile terminated oligomer was prepared by dissolving 20 grams of the resin in 200 ml of sulfolane. Then 10 grams of terephthalonitrile N,N'-dioxide was added to the solution and the mixture was stirred at room temperature for 48 hours. The resultant resin was isolated by triturating the reaction mixture with about 5 times its volume of absolute ethanol, filtering, and washing the precipitated product with fresh ethanol. The oligomer was then heated for 40 minutes at 230°-240° C. in a vacuum. It was dissolved in dimethylformamide, and the resulting lacquer was then applied to glass cloth reinforcement until the resin content was 40 percent. A multi-layer laminate was made by molding at 485°-525° F. under vacuum bag conditions.

EXAMPLE III

A solution of bis[4-(3-aminophenoxy)phenyl] ether (1.00 grams, 0.0026 mole) in 10 ml of dry dimethylformamide was added to a rapidly stirring solution of benzophenonetetracarboxylic dianhydride (1.68 grams, 0.00520 mole) in 10 ml of dimethylformamide. The solution was warmed to 65° C. for one hour. The heating was discontinued and solid 3-aminobenzonitrile (0.612 gram, 0.00520 mole) was added and the solution once more was heated for 16 hours at 75° C. The solvent was evaporated off with a rotary film evaporator and then 25 ml of acetic anhydride was added to the residue. The mixture then was heated at reflux for 2 hours. The acetic anhydride was evaporated off using a rotary film evaporator and the residue was washed with fresh ethanol. The product was dried in a vacuum oven at 80° C. and yielded 2.0 grams of product.

EXAMPLE IV

A solution of 1,3-di(3-aminophenoxy)benzene (12.0 grams, 0.041 mole) in 40 ml of dimethylformamide was added dropwise over a 50 minute period to a rapidly stirring solution of benzophenonetetracarboxylic dianhydride (26.3 grams, 0.082 mole) in 100 ml of dimethylformamide kept at 70° C. The reaction mixture was kept at 70°-75° C. overnight. To the mixture was added 3-aminobenzonitrile (10.2 grams, 0.086 mole) and the mixture heated just below reflux for 2 hours. The solvent was then removed on the rotary film evaporator and the resin imidized by treatment with acetic anhydride (200 ml). The mixture was heated at reflux overnight. The acetic anhydride was then removed on the rotary film evaporator and the solid residue was dispersed in absolute ethanol (800 ml), filtered and thoroughly washed with fresh ethanol. The resin was dried in a vacuum oven at 80° C. for 72 hours and yielded 31.4 grams of product.

We claim:
1. A compound of the following structure

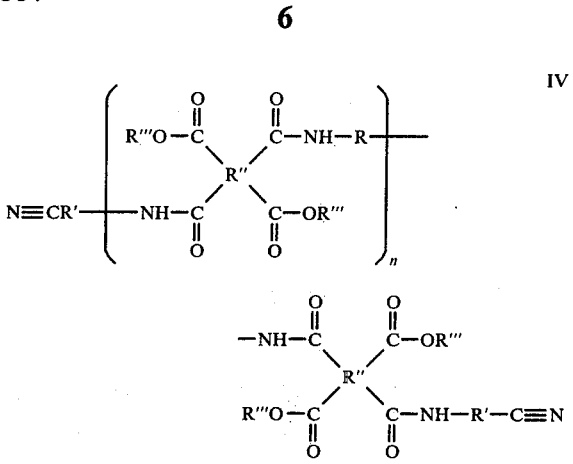

wherein R is arylene ether or arylene thioether, R' is arylene or arylene ether, n is an average from 1 to about 4, R'' is

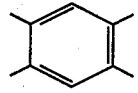

or

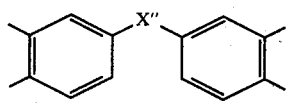

X'' is C=O, CH$_2$, O, S, or a bond and R''' is a lower alkyl.

2. A compound of claim 1 wherein n is an average of about 1.

3. A compound of claim 1 wherein R' is a phenylene.

4. A compound of claim 2 wherein each nitrile group is in meta position with respect to a ether or thioether linkage of R'.

5. A compound of claim 3 wherein R is

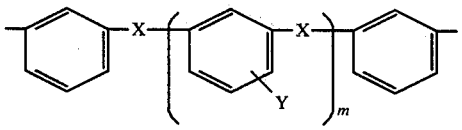

wherein X is O or S, Y is H or C≡N and m is a value from 0 to about 4.

* * * * *